United States Patent [19]

Boullet

[11] Patent Number: 4,830,126

[45] Date of Patent: May 16, 1989

[54] APPARATUS FOR THE AUTOMATIC MEASUREMENT OF THE APPARENT WEIGHT OF A SLUDGE CONTAINED IN A LIQUID AND SYSTEM FOR AUTOMATICALLY MEASURING THE PONSAR INDEX OF SUCH A SLUDGE, USING THE APPARATUS

[75] Inventor: Joseph Boullet, Nanteuil Le Haudouin, France

[73] Assignee: Commissariat a l'Energie Atomique, Paris, France

[21] Appl. No.: 205,285

[22] Filed: Jun. 10, 1988

[30] Foreign Application Priority Data

Jun. 12, 1987 [FR] France ............................ 87 08209

[51] Int. Cl.⁴ ................... G01G 5/02; G01G 19/40; G01N 9/00

[52] U.S. Cl. ............................. 177/207; 177/25.14; 73/444

[58] Field of Search ............... 177/25.14, 207; 73/444

[56] References Cited

U.S. PATENT DOCUMENTS

| | | | |
|---|---|---|---|
| 3,871,489 | 3/1975 | Patigalia ........................ | 177/207 X |
| 4,000,657 | 1/1977 | Ponsar .............................. | 73/444 X |
| 4,216,886 | 8/1980 | Puschalovsky et al. ........ | 177/207 X |
| 4,779,462 | 10/1988 | Boullet et al. .................. | 73/444 |

Primary Examiner—George H. Miller, Jr.
Attorney, Agent, or Firm—Oblon, Fisher, Spivak, McClelland & Maier

[57] ABSTRACT

An apparatus for automatically measuring the apparent weight of a sludge contained in a liquid and a system for automatically measuring the PONSAR index of such a sludge, using the apparatus. The apparent weight of a liter of clarified liquid is obtained by means of optoelectronic means (22, 106, 108) allowing the measurement of the difference between the two levels of clarified liquid in a reservoir (18), corresponding to the reaching therein of an equilibrium position by a flask (20) successively filled with sludge-charged liquid and clarified liquid respectively. Detection means (52, 54) allow the measurement of the volume of sludge decanted in half an hour in a test tube (28) filled with 1 liter of sludge-charged liquid and 1.5 liter of clarified liquid. Calculation of the volume-to-weight ratio then gives the PONSAR index.

Application to the operation of sewerage plants. FIG. 2.

14 Claims, 3 Drawing Sheets

APPARATUS FOR THE AUTOMATIC MEASUREMENT OF THE APPARENT WEIGHT OF A SLUDGE CONTAINED IN A LIQUID AND SYSTEM FOR AUTOMATICALLY MEASURING THE PONSAR INDEX OF SUCH A SLUDGE, USING THE APPARATUS

The invention relates to an apparatus for automatically measuring the apparent weight of a sludge contained in a liquid and a system for automatically measuring the PONSAR index of such a sludge, using the apparatus. The invention applies more particularly to the operation of sewerage plants operating on the activated sludge principle (biological purification).

French Patent No. 2,284,108 discloses a device for measuring the PONSAR index of a sludge contained in a liquid; a definition of this index will be given hereinafter. A device of the kind specified is also marketed by the HYDROCURE Company.

That device has the disadvantage of being manual, thus requiring a fairly prolonged and therefore expensive action of an operator.

French Patent Application No. 8,511,235 of July 23, 1985, referred to hereinafter as "document I" also discloses an apparatus for automatically measuring the apparent weight of a sludge contained in a liquid and a system for automatically measuring the PONSAR index of such a sludge, using the apparatus. The last-mentioned apparatus comprises an inductivity meter to determine the apparent weight of the sludge by inductance measurements.

It is an aim of the invention to obviate the aforementioned disadvantage by providing an apparatus for automatically measuring the apparent weight of a sludge contained in a liquid and a system for automatically measuring the PONSAR index of such a sludge, using such apparatus, which comprises optoelectronic means for measuring the apparent weight of the sludge, such means enabling an apparatus and system to be obtained which are simpler than those disclosed in document I.

More precisely the invention relates mainly to an apparatus for measuring the apparent weight of sludge contained in a liquid, characterized in that it comprises:

a receptacle;

a moving flask having a means enabling the flask to reach, from the bottom of the receptacle, which is filled with clarified liquid, two equilibrium positions corresponding to the flask filled with clarifying liquid and the flask filled with sludge-charged liquid respectively, the flask also being designed to rise, when filled with clarified liquid or sludge-charged liquid, in the receptacle filled with clarified liquid, only when the flash is submerged;

means for filling the flask with clarified liquid and sludge-charged liquid and for emptying the flask;

means for filling the receptacle with clarified liquid until the flask, filled with clarified liquid or sludge-charged liquid, has reached the corresponding equilibrium and emptying positions of the receptacle;

first optoelectronic detection means adapted to supply an electric signal in dependence on the level of clarified liquid in the receptacle; and an electronic processing system adapted to determine the apparent weight of a volume of sludge-charged liquid, weighed in the clarified liquid, from electric signals corresponding to the levels of the clarified liquid in the receptacle, when the flask is filled with sludge-charged liquid and clarified liquid respectively, by suitably controlling the means for filling and emptying the receptacle and the flask.

Preferably, the flask has a conical bottom which has a ballast and is continued in the upward direction by a cylindrical wall whose upper edge is slightly higher on the inside than on the outside of the flask. The conical bottom of the flask contributes towards the evacuation of air bubbles when the flask is immersed in the clarified liquid. The lowering of said edge is done to prevent the release of sludge-charged liquid from the flask when it is filled therewith and immersed in the clarified liquid of the receptacle during filling. The ballast is provided to prevent the flask filled with clarified liquid from rising in the receptacle in the course of filling before the submersion of the flask.

Also preferably the flask is made of a material which, when it is immersed in the clarified liquid, does not absorb such liquid but on the contrary is rapidly saturated therein. The words "material which is quickly saturated" mean a material which is saturated in a time $t$ which is very short in comparison with the time $t_1$ during which the flask remains in the clarified liquid of the receptacle ($t$ less than about 0.1 $t_1$, for example).

In an advantageous embodiment of the apparatus according to the invention it also comprises means for supporting the flask and limiting its movements in the direction of the top of the receptacle.

In an advantageous embodiment the apparatus according to the invention also comprises a probe with electrodes which is provided to inform the electronic processing system of the filling of the flask, the probe being displaceable and made rigidly integral with a duct provided for the filling and emptying of the flask.

To displace the probe under the duct, use can be made of a double-action jack (first jack).

In a preferred embodiment of the apparatus said means with which the flask is provided is a rod whose lower end is rigidly integral with the flask and whose length is such as to exceed the maximum level of clarified liquid capable of being contained in the receptacle.

Preferably the apparatus comprises second detection means provided to detect the reaching by the flask, filled with clarified liquid or sludge-charged liquid, of the corresponding equilibrium position, with a view to controlling the stoppage of the filling of the receptacle.

According to a possible feature of the invention the second detection means comprise a phototransmitter, a photodetector and said rod, and the upper end of the rod is adapted to deflect a light beam coming from the photo-transmitting means in the direction of the photodetector means when such upper end meets the light beam.

Also preferably the first detection means comprises a floater adapted to float in the receptacle on the surface of the clarified liquid when the receptacle contains the latter, a detector assembly comprising at least one phototransmitter and at least one photodetector made integral and disposed opposite one another on either side of the receptacle, the floater being opaque to the light which each phototransmitter is capable of transmitting, the receptacle being transparent to such light, and means for displacing the detector assembly which are adapted to displace the latter along the receptacle substantially from the top thereof and are controlled by the electronic processing system, the photodetector being adapted to inform the electronic processing system of the position of the floater.

The invention also relates to a system for measuring the PONSAR index of a sludge contained in a liquid, characterized in that it comprises:

the apparent weight measuring apparatus, which also forms part of the invention;

another receptacle;

means for filling the other receptacle with clarified liquid and sludge-charged liquid and for emptying such other receptacle;

third detection means adapted to supply other electric signals in dependence on the level of decanted sludge in the other receptacle previously filled with clarified liquid and sludge-charged liquid, and the electronic processing system is also adapted to determine, from such other signals, the volume of sludge decanted into the other receptacle, corresponding to a predetermined quantity of sludge-charged liquid, and also to determine the PONSAR index of the sludge, using the apparent weight and volume of decanted sludge, by suitably controlling the filling and emptying means.

According to a preferred embodiment of the measuring system according to the invention, the third detection means comprise another detector assembly comprising at least one phototransmitter and at least one photodetector made integral and disposed opposite one another on either side of the other receptacle, the latter and the clarified liquid being transparent to the light which each phototransmitter is capable of transmitting and the sludge being opaque to such light, and means for displacing such other detector assembly which are adapted to displace the latter along said other receptacle substantially from the bottom thereof, and are controlled by the electronic processing system, the photodetector of the other detector assembly being adapted to inform the electronic processing system of the position of the separation surface between the decanted sludge and the clarified liquid in the other receptacle.

Preferably, the predetermined quantity of sludge-charged liquid being the result of the addition to a given quantity of clarified liquid, reaching a first level in the other receptacle, of a given quantity of sludge-charged liquid reaching a second level in such other receptable, the measuring system also comprises another probe with electrodes which can be displaced between such first and second levels and is adapted to inform the electronic processing system of the liquid successively reaching such first and second levels, with a view to controlling the stoppage of the corresponding fillings.

Lastly, the measuring system according to the invention can also comprise another double-action jack provided to displace the other probe between the first and second levels.

Figure 1:
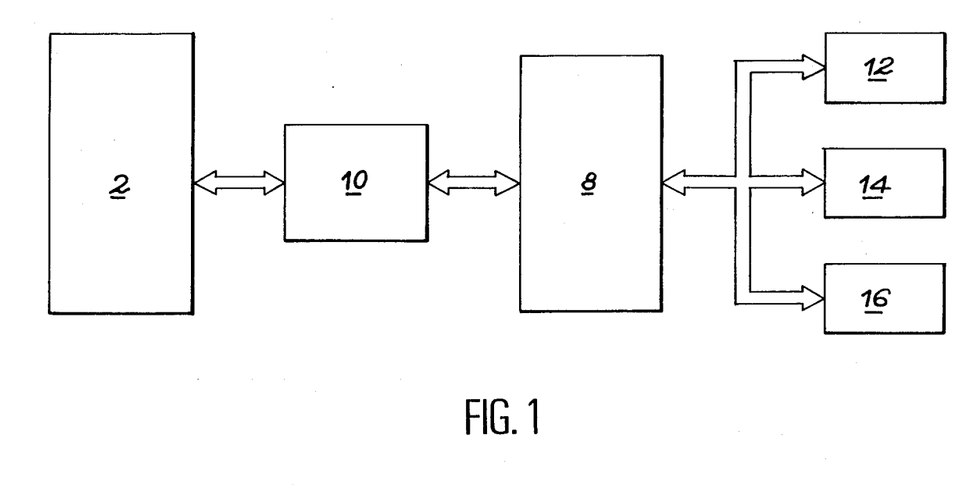
FIG. 1 is a diagrammatic view of a particular embodiment of the system for automatically measuring the PONSAR index to which the invention relates.

The invention will be better understood from the following description of purely indicative, non-limitative embodiments thereof with reference to the accompanying drawings, wherein:

FIG. 1 shows diagrammatically a particular embodiment of the system according to the invention adapted to automatically measure the PONSAR index.

This index, which enables the quality of the sludges of sewerage plants to be examined at all stages of the purification process, is defined as the V/V ratio, wherein P denotes the volume settling in half an hour (as a rule expressed in milliliters) - i.e., the volume of deposit obtained after the decantation for half an hour of one liter of sludge-charged liquid in one liter and a half of clarified liquid, P denoting the apparent weight (or more precisely the apparent mass), expressed in grams, of one liter of sludge-charged liquid weighed in the same clarified liquid.

The liquid is water in the case of a sewerage plant, which is taken as an example in what follows.

The system shown in FIG. 1 comprises:

an assembly 2 comprising a device 4 for measuring the volume V (FIG. 2) and a device 6 for measuring the weight P (FIG. 2); the assembly can be placed in a cupboard which can also contain a pump, solenoid valves and motors provided for the operation of such devices;

a computer assembly 8 provided to control the devices and calculate the PONSAR index, and a power interface 10 ensuring the connection between the computer assembly 8 and the assembly 2 of devices and cooperating with the computer assembly to form an electronic processing system.

The computer system 8 is also connected to a diskette reader 12 in which a programme is recorded which enables the automatic measuring system to operate, to a video monitor 14 enabling the results of the measurements performed to be displayed, and to a printer 16 enabling the outline of the results to be preserved.

Figure 2:
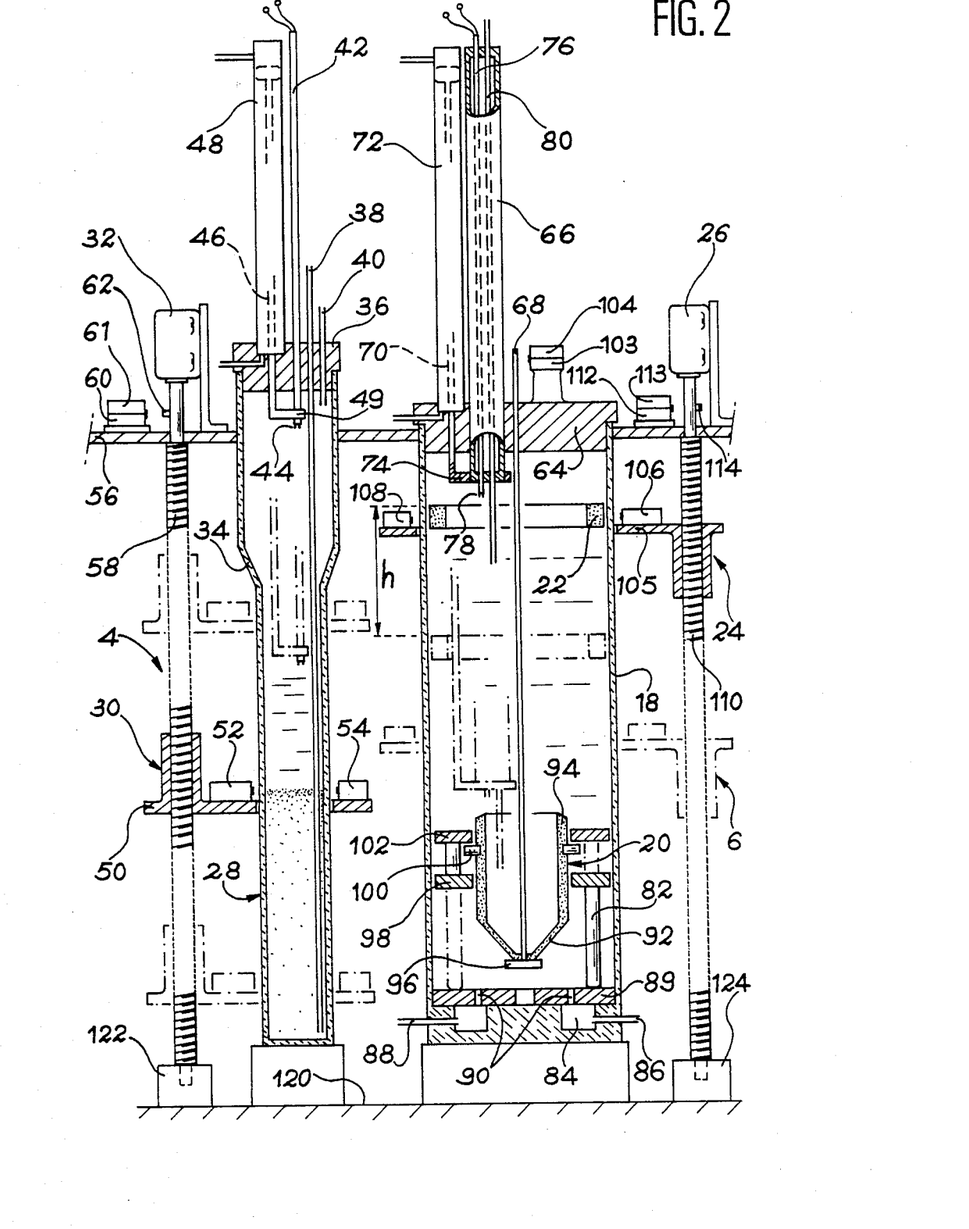
FIG. 2 is a diagrammatic view of a device for measuring the volume of sludge decanted and a device for measuring the apparent weight which form part of the system.

FIG. 2 shows diagrammatically the assembly 2 of the devices 4 and 6. The device 6, enabling the apparent weight to be measured, comprises an elongate receptacle 18 of large capacity, for example, of the order of 10 liters, hereinafter referred to as the "reservoir", and a flask 20, an annular floater 22 adapted to float in the reservoir when it contains clarified water, a detector assembly 24 and an asynchronous motor 26 provided to move the detector assembly 24 along the reservoir.

The device 4, enabling the volume of decanted sludge to be measured, comprises another elongnate receptacle 28, hereinafter referred to as the "test tube", which has a capacity of the order of, for example, three liters, and a detector assembly 30 and an asynchronous motor 32 provided to move the detector assembly 30 along the test tube.

The test tube has a flaired neck 34 enabling the sludge-charged water to flow gently on the neck, thereby facilitating the decanting of the sludge in the clarified water with which the test tube is to be filled.

Moreover, the test tube, which can be made of glass or plexiglass, is closed by a cover 36, for example, of plexiglass, which is formed with apertures through which there extend respectively: a tube 38 for emptying the test tube; a tube 40 for filling the test tube with clarified water and sludge-charged water; a tube 42 through which the electric supply extends of a probe with electrodes 44 attached to the lower end of the tube 42; and the rod 46 of a double-action jack 48 each end of which is formed with an aperture enabling it to be supplied with control fluid, for example, water.

That end of the tube 38 which is in the test tube is situated adjacent the end thereof, while the end of the tube 40 which is also in the test tube, is diposed above the test tube neck.

The jack 48 is so attached to the cover 36 that its rod can be moved parallel with the test tube axis. The tube 42, which is parallel with the jack rod and whose lower end is made rigidly integral with the lower end of the rod, for example, by means of a small plate 49, can also be moved in parallel with the test tube axis.

The travel of the hydraulic jack 48 is such that when the jack is in the bottom position, the lower end of each of the electrodes of the probe 44 comes to a level corresponding to one liter and a half of clarified water in the test tube 28, while when the jack is in the top position, such end corresponds to two and a half liters of water and sludge in the test tube 28.

The detector assembly 30 comprises an, for example, annular shelf 50 which encloses the test tube 28 and can be moved therealong. The tray 50 carries at least one transmitting photodiode 52, preferably a number of transmitting photodiodes, so oriented as to send light beams through the test tube 28, the latter and the clarified water being transparent to the light transmitted by the photodiodes. The shelf 50 also carries opposite the photodiodes 52 a photo-detector, such as a phototransistor 54, adapted to receive the light emitted by the photodiodes which has passed through the test tube 28 when it is not impeded by any sludge contained therein.

The asynchronous motor 32 is attached to a support 56 disposed in the upper portion of the test tube 28. The motor drives an endless screw 58 in rotation around an axis parallel with that of the test tube 28. The shelf 50 is coupled to the endless screw 58 so as to rise or descend along the test tube 28 in accordance with the direction of rotation of the motor 32.

The principle of measuring the volume of decanted sludge is as follows: after the test tube has been filled with one liter and a half of clarified water (something which is detected by the probe 44 when the jack 48 is in the bottom position), and then with one liter of sludge-charged water (something which is detected by the probe 44 when the jack 48 is in the top position), the assembly is allowed to decant for half an hour. The shelf is then moved upwardly in the test tube by a motor 32 (controlled by the electronic processing system), while the photodiodes emit rays of light. As soon as the rays of light meet the sludge, which is opaque thereto, they cannot reach the phototransistor. When the shelf reaches the level separating the water and the decanted sludge in the test tube, the rays of light can press through the test tube and reach the phototransistor, which then informs the electronic processing system of the fact. Then, if the pitch of the endless screw 58 is known, counting the number of revolutions performed by the motor 32 enables the level of mud decanted in the test tube to be determined, and if the section of the test tube is known, the volume of decanted mud to be determined.

To determine the number of revolutions performed by the motor 32, use is made of a detector assembly 60-61 comprising a phototransmitter 60 attached to the support 56 (through which the shaft of the motor 32 extends) and a photodetector 61 disposed on the phototransmitter, and also an optically reflecting finger 62 attached to the motor shaft and adapted to deflect a beam of light transmitted by the phototransmitter 60 in the direction of the photodetector 61 at each passage in front of the detector assembly 60-61, the photodetector 61 then generating an electric pulse, the number of electric pulses therefore being equal to the number of revolutions performed by the motor 32.

Returning to the device 6 for measuring the apparent weight, the reservoir 18, which can be made of glass or plexiglass, is closed by a cover 64, for example, made of plexiglass, formed with apertures through which there extend respectively: a rigid sheath 66; a rod 68 made rigidly integral with the flask 20, as will be shown in greater detail hereinafter; and the rod 70 of a double-action jack 72 so attached to the cover 64 that its rod can be moved in parallel with the axis of the reservoir. The jack 72 also has at each of its two ends an aperture for the supply of control fluid, for example, water, to the jack.

The sheath 66, which is parallel with the rod of the jack 72 and whose lower end is made integral with the lower end of the rod of the hydraulic jack 72 by means of a small plate 74, for example, can also be moved in parallel with such axis.

Attached inside the sheath 66 is a tube 76, through which the electric supply extends for a probe 78 with electrodes which is attached to the lower end of the tube 76, and a duct 80 via which the flask is supplied with clarified water and sludge-charged water and via which the flask is emptied. The upper end of the duct 80 is connected to one path of a fixed four-way distributor 116 via a flexible duct 81 (FIG. 3) long enough to withstand the movements of the sheath 66.

The tube 76 and the duct 80 are attached to each end of the sheath 66 by a ring, for example, of polyvinyl chloride.

If the device 6 is not used, the flask 20 rests on a support 82 adjacent the bottom of the reservoir 18. The electrodes of the probe 78 and the lower end of the duct 80 extend beyond the lower end of the sheath 66. The travel of the jack is such that when the jack is in the bottom position and the flask 20 rests on its support 82, the lower end of each electrode is at the level of the upper edge of the flask, so as to be able to detect the end of the filling of the flash with clarified water or sludge-charged water, the electrodes being adjacent the cover 64 of the reservoir when the jack is in the top position. The lower end of the duct 80 extends beyond the sheath 66 by a length such that when the jack is in the bottom position, such lower end of the duct 80 is adjacent the bottom of the flask.

The cover 64 and the cover 36 are also formed with apertures (not shown) enabling air to circulate between the inside and the outside of the receptacles 18 and 28.

The reservoir is filled with clarified water and emptied via its base. To prevent boiling phenomena during filling, the base of the reservoir is formed with an annular groove 84. Ducts 86 and 88 provided for the filling and emptying of the reservoir respectively discharge into such cavity, which communicates with the rest of the reservoir via apertures 90 of very small diameter (for example, of the order of 1 to 2 mm) extending through a plate 89 resting against the base of the reservoir.

The flask 20 is preferably made of polyethylene. Moreover, so as to allow the "sliding" and evacuation of air bubbles when the flask is immersed in the clarified water which the reservoir is to contain, the flask has a conical bottom 92 prolonged in the upward direction by a cylindrical wall 94 whose upper edge is slightly higher on the inside than on the outside of the flask (the inclination of such edge being, for example, of the order of 20° to 30° in relation to a plane perpendicular to the axis of the flask.

The flask also comprises a ballast 96 attached to its bottom outside the flask. The ballast is so selected that when the flask is placed on its support 82 and filled with clarified water, the flask starts to rise in the direction of the top of the reservoir during the filling only when the flask is submerged.

The support 82 of the flask comprises a collar 98 having feet enabling it to rest on the plate 89. The flask 20 has pins 100 enabling it to rest against the collar 98.

The support 82 is also designed to limit the movement of the flask. To this end the support 82 also comprises another collar 102 which is attached to the collar 98 and disposed at a sufficient distance thereabove to enable the flask filled with clarified water or sludge-charged water to reach the corresponding position of equilibrium in the reservoir containing clarified water, without the pins 100 abutting the other collar 102.

Preferably the collars are formed with holes to facilitate the passage of the clarified water during the filling of the reservoir.

The rod 68 is attached to the bottom of the flask and extends along its axis. As a variant, the ballast 96 can be attached to the lower end of the rod 68, which in that case extends through the bottom of the flask in sealing-tight relationship.

The length of the rod 68 is such that the rod emerges very slightly from the cover 64 of the reservoir. A ring, for example, of teflon, can be placed inside the aperture provided for the passage of the rod through the cover 64, to reduce friction taking place when the rod moves.

The various fillings and emptyings of the flask are performed when the flask is resting on its support, in which case the jack 72 is in the bottom position.

The detection of the flask having reached one or other of its equilibrium positions corresponding respectively to the flask filled with sludge-charged water or the flask filled with clarified water is performed by means of a detector assembly 103-104 comprising a phototransmitter 103 surmounted by a photodetector 104, the detector assembly being so attached to the cover 64 of the reservoir that it is at a distance of the order of several centimetres from the upper end of the rod 68 when the flask rests on its support, such distance being in fact smaller than that separating the two collars of the support 82.

The photodetector 104 is adapted to sense the light beam generated by the phototransmitter 103 and reflected by the, for example, polished stainless steel rod 68, when the upper end of the rod 68 reaches the level of the assembly 103-104 due to the flask having reached an equilibrium position in the reservoir during filling. The photodetector 104 then delivers a signal. The electronic processing system, informed by such signal that the equilibrium position in question has been reached, controls the stoppage of the filling of the reservoir with clarified water.

The detector assembly 24 is designed like the detector assembly 30 and therefore comprises a, for example, annular shelf 105 which encloses the reservoir 18 and can be moved therealong. The shelf 105 carries at least one emitting photodiode 106, preferably a number of emitting photodiodes, so oriented as to deliver light beams through the reservoir 18, which is transparent to the light emitted by each photodiode 106. The shelf 105 also carries opposite the photodiode 106 a photodetector, such as a phototransistor 108, which is adapted to receive the light emitted by the photodiodes 106 which has passed through the reservoir 18, as long as it is not impeded by the floater 22, which is opaque to such light, and which informs the electronic processing system of the fact.

The asynchronous motor 26 is attached at the cover 64 of the reservoir, on a support; the test tube/reservoir assembly can be so designed that this support is the support 56 of the motor 32. The motor 26 drives an endless screw 110 in rotation around an axis parallel with the axis of the reservoir, such endless screw controlling the rise or descent of the shelf 105 along the reservoir in dependence on the direction of rotation of the motor 26.

These movements take place substantially from the top of the reservoir, for example, and are controlled by the electronic processing system. If the pitch of the endless screw 110 and the number of revolutions are known, the electronic processing system can determine (and memorize) the level reached by the floater 22.

The number of revolutions performed by the motor 26 is determined by means of a detector assembly 112-113 attached to the support of the motor 26. The motor spindle has a finger 114 disposed at the level of the detector assembly 112-113. The latter comprises a phototransmitter 112 surmounted by a photodetector 113 adapted to transmmit an electric pulse at each passage of the finger 114 in front of the detector assembly 112-113, the photodetector 113 then receiving the beam of light transitted by the photoransmitter 112 and reflected by the finger 114 in the direction of the photodetector 113. The pulses delivered by the photodetector and corresponding to the revolutions performed by the motor 26 are then counted by the electronic processing system, which is thus informed of the number of revolutions of the motor 26.

The principle of measuring the apparent weight is as follows: the apparent weight is proportional to the difference in immersion h in the reservoir filled with clarified water of the flask 20 filled with a sludge-charged water and clarified water respectively. The difference in immersion h is equal to the difference between the levels of clarified water in the reservoir (i.e., to the difference between the positions of the floater 22) corresponding to the equilibrium positions of the flask filled with sludge-charged water and the flask filled with clarified water respectively. More precisely, the apparent weight P is connected with the difference in immersion h by the following formula:

$$P = h \cdot S \cdot v^{-1} \cdot d \cdot g$$

where S, V, d and g denote the section of the rod 68, the useful volume of the flask (the contents of the flask which, for example, are equal to 0.5 liter), the volumetric mass of the clarified water and gravitational acceleration respectively.

In fact, the apparent weight (for a liter of sludge-charged water) is expressed in grams, so that the quantity g in the above formula is ignored.

The advantage of the flask being made of polyethylene is that this material is rapidly saturated in water, so that the weight of the flask is constant in the two phases of measuring the apparent weight (flask filled with sludge-charged water, and flask filled with clarified water).

The flask can also be made of glass which, in contrast, does not absorb water when it is immersed therein, the weight of the flask remaining just as constant in that case.

Figure 3:
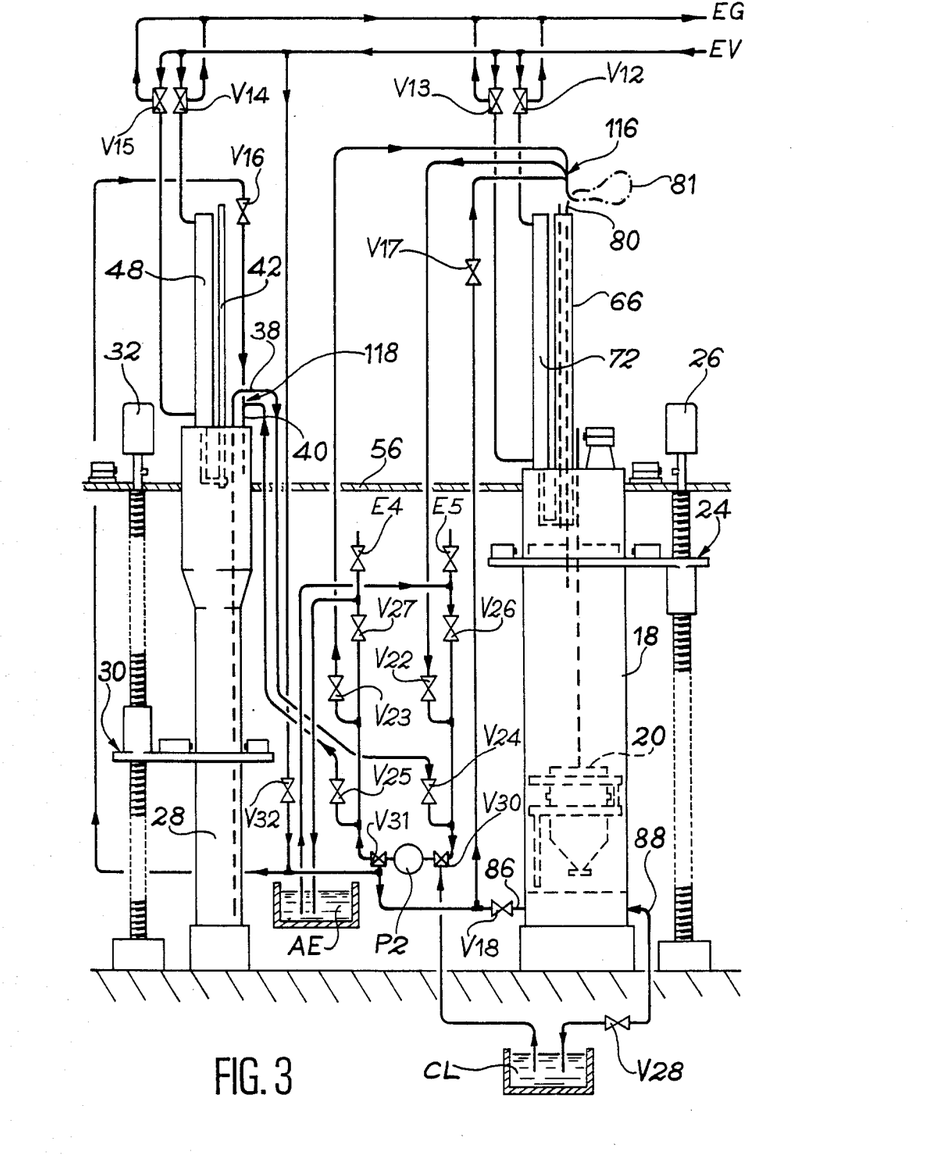
FIG. 3 is a diagrammatic view of the hydraulic circuits of the system.

Measurement of the quantities P and V requires the filling of the test tube with clarified water and sludge-charged water and the emptying of the test tube, and also the filling of the reservoir with clarified water and the emptying of the reservoir, as well as the filling of the flask with clarified water and sludge-charged water, and also the emptying of the flask. These various fillings and emptyings are peformed by means of a single hydraulic assembly combining two hydraulic circuits called the "clarified water circuit" and the "sludges circuit" respectively. The source of clarified water is formed by the clarifier CL of the purification station, while the source of sludge-charged water is formed by the aerator AE of the purification station.

The sludges circuit is as follows:

The sludge-charged water is pumped into the aerator AE by a pump P2. A conduit extends from the aerator and terminates in one path of a two-way solenoid V26. Three derivations are connected in parallel to the second path of this solenoid:

a first derivation terminating in one path of a two-way solenoid V22 whose second path terminates in a first path of a four-way distributor 116, whose second path is connected to the duct 80 via a flexible duct 81;

a second derivation terminating in one path of a two-way solenoid V24 whose second path is connected to the duct 38; and a third derivation connected to a first path of a three-way solenoid V30 whose second path terminates in the inlet of the pump.

The outlet of the pump P2 is connected to a first path of a three-way solenoid V31. A second path thereof is connected to one path of a two-way solenoid V27 whose second path is connected to the aerator.

Disposed successively on the conduit connecting the pump P2 to the solenoid V27, counting from the pump P2, are the following:

a first derivation terminating in one path of a two-way solenoid V25 whose second path is connected to a first path of a three-way distributor 118 whose second path is connected to the conduit 40; and a second derivation terminating in one path of a two-way solenoid V23 whose second path is connected to the third path of the distributor 116.

For the sludges circuit, therefore, we have the following different conditions, the solenoids being opened or closed for each condition correspondingly:

stand-by: from AE to V26 to V30 to P2 to V31 to V27 to AE filling the flask with sludge-charged water: AE to V26 to V30 to P2 to V31 to V23 to distributor 116 filling the test tube with sludge-charged water: AE to V26 to V30 to P2 to V31 to V25 to distributor 118 emptying the test tube: from the duct 38 to V24 to V30 to P2 to V31 to V27 to AE emptying the flask: from the conduit 80 to the distributor 18 to V22 to 30 to P2 to V31 to V27 to AE.

Vents are also provided by solenoids E4 and E5 respectively mounted in derivation on the conduits connecting the solenoid V26 and the solenoid V27 to the aerator.

The clarified water circuit comprises a solenoid V30 whose third path is connected via a duct to the clarifier, the pump P2 and the solenoid V31. Four derivations are connected in parallel to the third path of the solenoid V31;

a first derivation terminating in one path of a two-way solenoid V16 whose second path is connected to the third path of the distributor 118;

a second derivation terminating in one path of a two-way solenoid V17 whose second path is connected to the fourth path of the distributor 116;

a third path terminating in a path of a two-way solenoid V18 whose second path is connected to the duct 86; and a fourth path terminating in one path of a two-way solenoid V32 whose second path terminates, as will be seen hereinafter, in a "mains water" circuit (clean pressurized water supplied by a town water distributing network).

The clarified water can therefore be sucked by the pump P2 into the clarifier CL through the solenoid V30 and distributed by the solenoid V31, respectively and as required;

into the flask 20 via V17,
into the test tube 28 via V16, and
into the reservoir 18 via V18.

The clarified water capable of being contained in the reservoir 18 is emptied by gravity from the duct 88 in the direction of the clarifier through a two-way solenoid V28.

As already indicated, the clarified water contained in the flask (or test tube respectively) is emptied via the sludges circuit by means of the pump P2 and the solenoid V22 (and V24 respectively).

There is a third circuit enabling mains water to be used, for example, to proceed after a measurement to the rinsing of the circuits the flask, the test tube and the reservoir. The filling of these latter with mains water is performed via the two-way solenoid V32 whose second path is connected to the mains water supply conduit EV. Emptying the reservoir is performed by gravity by means of V28, the test tube or the flask being emptied by using the sludges circuit, as indicated hereinbefore.

The mains water is also supplied to the two jacks via three-way solenoids V12, V13, V14 and V15, to enable the jacks to operate.

More precisely, the mains water is delivered in parallel to the respective inlets of the solenoids V12, V13, V14 and V15. The three-way solenoid V12, used for moving the jack 72 into the bottom position, has one of its two outputs connected to the orifice of the jack 72, corresponding to the jack's being moved into the bottom position. The three-way solenoid V13, used for moving the jack 72 into the top position, has one of its two outputs connected to the aperture of the jack 72, corresponding to the moving of the jack into the top position.

The three-way solenoid V14, used for moving the jack 48 associated with the test tube into the bottom position, has one of its two outputs connected to the aperture of the jack 48, corresponding to the moving of the jack 48 into the bottom position. The solenoid V15, used for moving the jack 48 into the top position, has one of its two outputs connected to the aperture of the jack 48, corresponding to the moving of the jack 48 into the top position.

The second output paths of the three-way solenoids V12, V13, V14 and V15 are connected to a conduit terminating in drain channel EG.

It will be noted that the devices 4 and 6 rest on a common frame 120 on which the respective bearings 122 and 124 of the endless screws 58 and 110 also rest.

The power interface 10 (FIG. 1), whose contents are not shown, comprises an assembly of relays for controlling the solenoids and the motors 26 and 32, electronic circuits respectively associated with the probes 44 and 78 with electrodes, relay circuits enabling the detector assemblies 52–54, 103–104 and 106–108 respectively to be connected to the computer assembly 8, two relay circuits respectively associated with the detector asemblies 60–61 and 112–113, and lastly various supplies for providing the voltages and currents required for the operation of the electronic system and the electric elements of the cupboard containing the devices 4 and 6.

The computer assembly 8 (FIG. 1) comprises a computer associated with an input-output card (not shown). The signals (O or 5V) coming from the input-output card cannot directly control the solenoids or the motors 26 and 32. Such control is therefore performed via the aforementioned relays (power relays) which are able to switch considerable currents and high voltages (cf. document I). Each of the motors 26 and 32 is controlled by two relays corresponding to the two directions of rotation of the motor respectively.

Moreover, unlike the other solenoids of the measuring system shown in FIG. 3, the solenoids E4 and E5, which enable the conduits on which they are mounted to be "emptied", during the stoppage of the measuring system, are not associated with power relays, but are supplied (closed) as soon as the measuring system is energized and opened as soon as the measuring is deenergized (not used).

The control of the solenoids V16, V17, V18, V22, V23, V24, V25, V26, V27, V28, V30, V31 and V32 causes no particular problem.

The three-way solenoids V12, V13, V14 and V15 are suitably (and conventionally) controlled for the proper operation of the jacks with which they are associated: for a given operating jack, one of the solenoids associated therewith must allow water to enter the jack, while the other associated solenoid must allow water to be evacuated from the jack.

It will be noted that the solenoid V27 must be closed by the opening of the solenoid V23 or of the solenoid V25 and that when the solenoids V23 and V25 are closed, the solenoid V27 must be opened. These conditions are put into effect from a lobic OR gate.

Similarly, when the solenoid V26 is opened, the two solenoids V22 and V24 must be closed, and the opening of one or other of the solenoids V22 and V24 must cause the closure of the solenoide V26. These conditions are put into effect from a logic OR gate.

The photodetector 54 controls a relay circuit whose output is connected to the computer assembly and which informs the latter that the shelf 50 has reached the level of separation of the water and the decanted sludge in the test tube.

The photodetector 108 also controls a relay circuit whose output is connected to the computer assembly and which informs the latter of the position of the floater 22.

Similarly, via a relay circuit the photodetector 104 informs the computer assembly 8 that the flask has reached each of its equilibrium positions.

The pulses generated by each photodetector 61 or 113 are supplied via a relay circuit to the electronic processing system, in which they are counted.

The detection probes 44 and 78 with electrodes can be constructed like the probe 66 in document I. Thus, the electrodes of each of the probes 44 and 78 can be connected to the computer assembly via a circuit of the kind shown in FIG. 13 of document I.

To prevent the pump P2 from idling, the emptying time of the test tube is programmed, so that no emptying sensor is required for the test tube. The "top" and "bottom" positions of each of the shelves 50 and 105 are detected by four microcontacts (one per position and per shelf—not shown), each of them being adatped to supply an indication O or 5V directly to the computer assembly.

The programme for managing the system for automatically measuring the PONSAR index, to which the invention relates, first of all comprises a stage of initializing the inputs-outputs of the computer assembly, followed by a check on the "starting position" of the device for measuring the volume and the device for measuring the apparent weight:

the probe associated with the jack corresponding to the test tube is checked to ensure that there is no water at the level of the probe, otherwise the test tube is emptied;

a check is made that the shelf corresponding to the reservoir is in the top position, otherwise it is put into that position;

a check is made that the shelf corresponding to the test tube is in the bottom position, otherwise it is put into that position;

a check is made that the jack corresponding to the reservoir is in the top position, otherwise it is put into that position; and a check is made that the jack corresponding to the test tube is in the bottom position, otherwise it is put into that position.

Then the following successive phases ("measuring process") of the management programme are formed:

1.—emptying of the reservoir (between two utilizations of the measuring system according to the invention, it is preferable to fill the reservoir enough for the flask at its base to be submerged)

2.—cleaning (i.e., filling with clarified water), then emptying (of the reservoir and test tube)

3.—filling of the test tube with clarified water (1.5 liters)

4.—ascent of the test tube jack

5.—filling of the test tube with sludge-charged water (1 liter) and triggering a delay (waiting time) of 30 minutes 6.—descent of the reservoir jack 7.—emptying of the flask 8.—filling of the flask with sludge-charged water 9.—filling of the reservoir with clarified water up to the top edge of the flask 10.—waiting for a predetermined time (equal to 3 or 4 minutes) for the decantation of the sludges into the flash (to prevent them from escaping when the flask is submerged)

11.—reascent of the reservoir jack

12.—filling of the reservoir with clarified water until the flask starts to move and reaches its equilibrium position.

13.—descent of the reservoir shelf

14.—reading of the water level in the reservoir and display of the result

15.—reascent of the reservoir shelf

16.—emptying of the reservoir until the water level therein is lower than the top edge of the flask 17.—descent of the reservoir jack 18.—emptying of the flask 19.—filling of the flask with clarified water (with a view to cleaning it)
20.—emptying of the flask
21.—filling of the flask with clarified water
22.—reascent of the reservoir jack
23.—filling of the reservoir with clarified water until the flask moves and reaches its equilibrium position
24.—descent of the reservoir shelf
25.—reading of the water level in the reservoir and displaying of the result
26.—reascent of the reservoir shelf
27.—total emptying of the reservoir
28.—descent of the reservoir jack
29.—emptying of the flask
30.—calculation of the apparent weight of the sludges, displaying of the result, then waiting for the end of the delay period of 30 minutes
31.—ascent of the test tube shelf
32.—reading of the level of sludge/clarified water separation in the test tube
33.—descent of the shelf for its repositioning
34.—calculation of the decantation volume and the displaying thereof, calculation of the PONSAR index and the displaying thereof
35.—emptying of the test tube
36.—filling of the test tube with mains water (2.5 liters) for cleaning the test tube
37.—emptying of the test tube
38.—descent of the test tube jack into the bottom position
39.—filling of the flask with mains water for cleaning the flask
40.—reascent of the reservoir jack
41.—filling of the reservoir jack with mains water until the flask is submerged
42.—stoppage of the programme.

As indicated in document I, a subprogramme enables the waiting times to be chronometered.

The end of the stages 9 and 16 is also detected by "chronometry" by means of this subprogramme, which also allows the chronometry of the flask and test tube emptying times.

Moreover, after determining the number N of revolutions performed by the motor associated with the test tube, the computer calculates the volume of decanted sludge V by the following formula:

$$V = (p.s.N) + VO$$

where p and s denote the pitch of the endless screw associated with the test tube and the cross-section of the test tube (between the bottom and the neck 34 of the test tube) respectively. The quantity VO is an initial volume due to the fact that the self associated with the test tube does not start precisely from a zero value. The quantity VO can be determined during the calibration of the automatic measuring system.

What is claimed is:

1. An apparatus for measuring the apparent weight of a sludge contained in a liquid comprising:
   a receptable (18):
   a moving flask (20) having a means (68) enabling the flask to reach, from the bottom of the receptacle, which is filled with clarified liquid, two equilibrium positions corresponding to the flask filled with clarified liquid and the flask filled with sludge-charged liquid respectively, the flask also being designed to rise, when filled with clarified liquid or sludge-charge liquid, in the receptacle filled with clarified liquid, only when the flask is submerged;
   means for filling the flask (20) with clarified liquid (P2 V17) and for filling the flask with sludge-charged liquid (P2 V23) and for emptying (P2 V22, V27) the flask (20);
   means for filling the receptacle (18) with clarified liquid (P1, V18) until the flask, filled with clarified liquid or sludge-charged liquid, has reached the corresponding equilibrium position and for emptying (V28) the receptacle;
   first detection means (22, 26, 106, 108, 110) which are of the optoelectronic type and able to supply an electric signal which is a function of the level of clarified liquid in the receptacle (18); and
   an electronic processing system (8, 10) for determining the apparent weight of a volume of sludge-charged liquid, weighed in the clarified liquid, from electric signals corresponding to the levels of the clarified liquid in the receptacle (18), when the flask (20) is filled with sludge-charged liquid and clarified liquid respectively, by suitably controlling the means for filling and emptying the receptacle and the flask.

2. An apparatus according to claim 1, wherein the flask (20) has a conical bottom (92) which has a ballast (96) and is continued in the upward direction by a cylindrical wall (94) whose upper edge is slightly higher on the inside than on the outside of the flask.

3. An apparatus according to claim 1, wherein the flask (20) is made of a material which, when it is immersed in the clarified liquid, either does not absorb such liquid or is rapidly saturated therein.

4. An apparatus according to claim 1, wherein it also comprises means (98, 102) for supporting the flask and for limiting its movements in the direction of the top of the receptacle (18).

5. An apparatus according to claim 1, wherein it also comprises a probe with electrodes (78) for informing the electronic processing system (8, 10) of the filling of the flask (20), the probe being displacable and made rigidly integral with a duct (80) intended for the filling and emptying of the flask.

6. An apparatus according to claim 5, wherein it comprises a first double-action jack (72) for displacing the probe (78) and the duct (80).

7. An apparatus according to claim 1, wherein said means with which the flask is provided is a rod (68) whose lower end is rigidly integral with the flask (20) and whose length is such as to exceed the maximum level of clarified liquid capable of being contained in the receptacle (18).

8. An apparatus according to claim 1, wherein it comprises second detection means (68, 103, 104) for detecting the reaching by the flask (20), filled with clarified liquid or sludge-charged liquid, of the corresponding eqilibrium position, with a view to controlling the stoppage of the filling of the receptacle (18).

9. An apparatus according to claims 7 or 8, wherein the second detection means comprises (103), photoemitter means, photodetector means (104) and said rod (68), and wherein the upper end of the rod (68) is adapted to deflect a light beam coming from the photoemitter means (103) in the direction of the photodetector means (104) when said upper end meets the light beam.

10. An apparatus according to claim 1, wherein the first detection means comprise a floater (22) adapted to float in the receptacle (18) on the surface of the clarified liquid when the receptacle contains the latter, a detector assembly comprising at least one (106) photoemitter and at least one photodetector (108) made integral and disposed opposite one another on either side of the receptacle, the floater being opaque to the light which each phototransmitter is capable of emitting, the receptacle being transparent to such light, and means (26, 110) for displacing the detector assembly which are able to displace the latter along the receptacle substantially from the top thereof and are controlled by the electronic processing system (8, 10), the photodetector being intended for informing the electronic processing system of the position of the floater.

11. A system for measuring the PONSAR index of a sludge which is contained in a liquid, wherein it comprises:

the apparent weight measuring apparatus according to claim 1;

another receptacle (28);

means for filling (28) with clarified liquid (P2, V16) and filling with sludge-charged liquid (P2, V25, V26) and emptying (P2, V24, V27) said another receptacle (28);

third detection means (32, 52, 54, 58) able to supply other electric signals which are a function the level of decanted sludge in said other receptacle (28) previously filled with clarified liquid and sludge-charged liquid, and wherein the electronic processing system (8, 10) also serves to determine, from said other signals, the volume of sludge decanted into said other receptacle, corresponding to a predetermined quantity of sludge-charged liquid, and also to determine the PONSAR index of the sludge, using the apparent weight and volume of decanted sludge, by suitably controlling the filling and emptying means.

12. A system according to claim 11, wherein the third detection means comprise another detector assembly comprising at least one (52) photoemitter and at least one photodetector (54) made integral and disposed opposite one another on either side of said another receptacle (28), the latter and the clarified liquid being transparent to the light which each photoemitter is capable of transmitting and the sludge being opaque to such light, and means (32, 58) for displacing other detector assemblies which are able to displace the latter along said other receptacle (28) substantially from the bottom thereof, and are controlled by the electronic processing system (8, 10), the photodetector of said other detector assembly being intended for informing the electronic processing system of the position of the separation surface between the decanted sludge and the clarified liquid in said other receptacle.

13. A system according to claim 11, wherein the predetermined quantity of sludge-charged liquid is the result of the addition to a given quantity of clarified liquid, reaching a first level in said other receptacle (28), of a given quantity of sludge-charged liquid reaching a second level in said other receptacle (28), and the measuring system also comprises another probe (44) with electrodes which can be displaced between said first and second levels and is intended for informing the electronic processing system (8, 10) of the liquid successively reaching said first and second levels, with a view to controlling the stoppage of the corresponding fillings.

14. A system according to claim 13, wherein it also comprises another double-action jack (48) for displacing said other probe (44) between the first and second levels.

* * * * *